(12) United States Patent
Venkatesh et al.

(10) Patent No.: US 6,471,747 B1
(45) Date of Patent: Oct. 29, 2002

(54) METHOD AND APPARATUS FOR DELIVERING AND RECOVERING GASSES

(75) Inventors: Arvind Venkatesh, Boston; Mitchell S. Albert, Cambridge, both of MA (US); Jeffrey J. Spiegelman, LaJolla, CA (US)

(73) Assignees: The Brigham and Women's Hospital, Inc., Boston, MA (US); Trustees of Boston University, Boston, MA (US)

( * ) Notice: Subject to any disclaimer, the term of this patent is extended or adjusted under 35 U.S.C. 154(b) by 0 days.

(21) Appl. No.: 09/598,428

(22) Filed: Jun. 20, 2000

(Under 37 CFR 1.47)

Related U.S. Application Data

(60) Provisional application No. 60/140,054, filed on Jun. 21, 1999.

(51) Int. Cl.[7] .................... A61B 5/055; B01D 51/00
(52) U.S. Cl. .................... 95/90; 95/117; 96/134; 96/142; 96/223; 55/DIG. 9; 324/300; 600/431
(58) Field of Search .................... 96/108, 134, 136, 96/142, 223, 225; 95/90, 117, 130; 55/DIG. 9; 324/300; 424/9.3; 600/431

(56) References Cited

U.S. PATENT DOCUMENTS

| | | | |
|---|---|---|---|
| 3,976,050 A | * | 8/1976 | Glasser et al. |
| 4,093,429 A | | 6/1978 | Siegler et al. |
| 4,156,811 A | | 5/1979 | Born .................... 250/284 |
| 4,202,345 A | * | 5/1980 | Farella et al. |
| 4,264,340 A | * | 4/1981 | Sircar et al. |
| 4,264,567 A | | 4/1981 | Pinto .................... 423/359 |
| 4,681,602 A | * | 7/1987 | Glenn et al. |
| 4,793,358 A | * | 12/1988 | Kimura et al. |
| 4,844,715 A | | 7/1989 | Henrich et al. |
| 5,980,608 A | * | 11/1999 | Dietz et al. ............ 95/133 |

OTHER PUBLICATIONS

Frossati, "Polarization of $^3$He, $D_2$ and (eventually) $^{129}$Xe Using Low Temperatures and High Magnetic Fields," *J. Low Temp. Physics* 111:521–532 (1998).

International Search Report for PCT/US00/17009 (Oct. 2000).

* cited by examiner

*Primary Examiner*—David A. Simmons
*Assistant Examiner*—Frank M. Lawrence
(74) *Attorney, Agent, or Firm*—Michael A. Sanzo; Fitch, Even, Tabin & Flannery

(57) ABSTRACT

The present invention is directed to a procedure for recycling used gasses and to devices that can be use to accomplish this recycling.

15 Claims, 1 Drawing Sheet

METHOD AND APPARATUS FOR DELIVERING AND RECOVERING GASSES

CROSS REFERENCE TO RELATED APPLICATIONS

The present application claims priority under 35 U.S.C 119(e) the U.S. provisional application No. 60/140,054 filed on Jun. 21, 1999.

STATEMENT OF GOVERNMENT SUPPORT

The work leading to this invention was supported by one or more grants from the U.S. Government. The U.S. Government therefore has certain rights in the invention.

FIELD OF THE INVENTION

The present invention relates to the recovery and recycling of gasses. The methods and devices disclosed are useful in a number of applications including MRI, MR spectroscopy, nuclear medicine scans, computerized tomography scans, PET scans and in anesthesiology.

BACKGROUND OF THE INVENTION

The value of MRI as a diagnostic tool for respiratory problems can be greatly enhanced if, before imaging, a person inhales a noble gas that has been put into a hyperpolarized state. Unfortunately, the future of hyperpolarized gas imaging is threatened by the limited availability of appropriate noble gasses, primarily $^3$H and $^{129}$Xe, and their high cost (Frosatti, et al., *J Low Temp. Phys.* 111:521–532 (1998)). Thus, it would be highly advantageous to have a system that can be used to recover and recycle used noble gasses for later use. Ideally, such a system would also be compatible with the recovery of other gasses in a wide variety of applications.

SUMMARY OF THE INVENTION

The present invention is based, in its first instance, upon the development of a novel system for extracting hyperpolarized noble gas (including $^3$He and xenon) after it has been has been administered to a patient undergoing an MRI imaging procedure. The gas is purified and recycled back to the hyperpolarized gas generator or stand-alone pressurized gas source. The system may also be advantageously employed to recover other types of gasses from a variety of sources. For example, it can be used to recover gasses used in connection with medical procedures such as MRI, MR spectroscopy, nuclear medicine scans, computerized tomography scans, PET scans and in anesthesiology. In addition, gasses used for veterinary purposes or in connection with the imaging of materials could be recovered. Examples of gasses that can be recovered include any isotope of Xe; any isotope of He; $^{31}$P; $^{13}$C; $^{23}$Na; and $^{19}$F.

In a first embodiment, the invention is directed to a method for recycling a chosen gas after it has been used in, preferably, a medical procedure. For example, a noble gas may be recycled after having been used in diagnostic MRI imaging. The method begins when a mixture containing the chosen gas is collected and introduced into a recycling system. For example, a patient that has undergone MRI imaging may exhale noble gas into a container which is connected to (or may subsequently be connected to) a recycling system. This system has a pump that passes the collected gas through a series of components, e.g., dryers, filters, getters, and sterilizers, designed to purify the chosen gas. Once purified, the chosen gas is transferred to a storage container where it may be maintained until needed. Upon demand, the stored gas is released and, optionally, mixed with other gasses. The mixture may then be passed into a system component designed to prepare it for administration to a second patient. For example, a noble gas may be introduced into a polarizing chamber where it is put into a hyperpolarized state prior to MRI. Finally, the prepared gas is delivered to a new subject, either directly, or by first introducing into a portable container. This system may be used in connection with any gas and with any of the medical procedures discussed above. In one preferred embodiment, a hyperpolarized gas is continually transported to and from a person during an MRI process. Typically, this will be accomplished by delivering the gas to the person through a port in the bore of the scanner of the machine used for MRI.

In another embodiment, the invention is directed to a device (see, for example, FIG. 1) with multiple components for recycling a chosen gas, e.g. a noble gas. The device may include a first portable container (102) for gas retrieved, e.g. from a patient. This container may be connected to one end of a first gas line and a vacuum pump (106) is connected to the second end. There is a getter (112) connected to the vacuum pump and a storage container (118) is connected to the getter. The design allows the vacuum pump to evacuate the gas from the first portable container and then pass it through the getter and into the storage container. One end of a second gas line is also connected to the storage container and its other end to a mass flow controller (120) for regulating the amount of gas that flows out of storage. The mass flow controller is connected to a purifier (122) which, in turn, is connected to a cell (126) for preparing the gas for future use, e.g., for transforming a noble gas into a hyperpolarized state. Finally, the cell may be connected to a second portable container (124) for receiving the prepared gas. Additional components that may be part of the device include: a dryer (108) connected to the vacuum pump (106); a second purifier (110) connected to the dryer (108) and to the getter (112); a sanitizer (131) for sterilizing gas, which is connected to the getter (112) and to the storage tank (118); a compressor (116) connected to the getter (116) and to the storage tank (118); a surge tank (104) connected to the first portable container (102) and to the vacuum pump (106); a valve (114) for introducing additional gas into the storage tank (118), which is connected to the sanitizer (131) and to the compressor (116); and a second storage tank (130) that may be used to mix additional gasses with chosen gas, which is connected to the purifier (122) and to the mass flow controller (120). In its most preferred form, the device comprises all of the elements discussed above arranged as shown in FIG. 1.

It will be apparent to one of skill in the art that certain of the components of the device described above may be rearranged without substantially interfering with its overall performance. Devices having only nonsubstantive changes of this type are encompassed as part of the invention.

In another embodiment, the invention is directed to a device for recycling a chosen gas, comprising: means for retrieving a mixture of gasses containing the chosen gas and introducing this mixture into the device; means for propelling the gas through the device; means for purifying the chosen gas as it is propelled through the device; means for storing purified gas; means for removing gas from storage and for regulating flow from storage; means for preparing gas for future use; and means for transferring the prepared gas out of said device. In one preferred embodiment, the chosen gas is a noble gas that is prepared for future use by putting it into a hyperpolarized state. The device may be incorporated into an MRI imaging machine and positioned in such a manner that the retrieval of used gas occurs at an exit port in the bore of the scanner of the MRI machine and gas is transferred out of the device at an entry port in the bore of the scanner of the MRI machine.

Finally, the invention includes methods for recycling a chosen gas through the use of any of the devices described herein.

Figure 1:
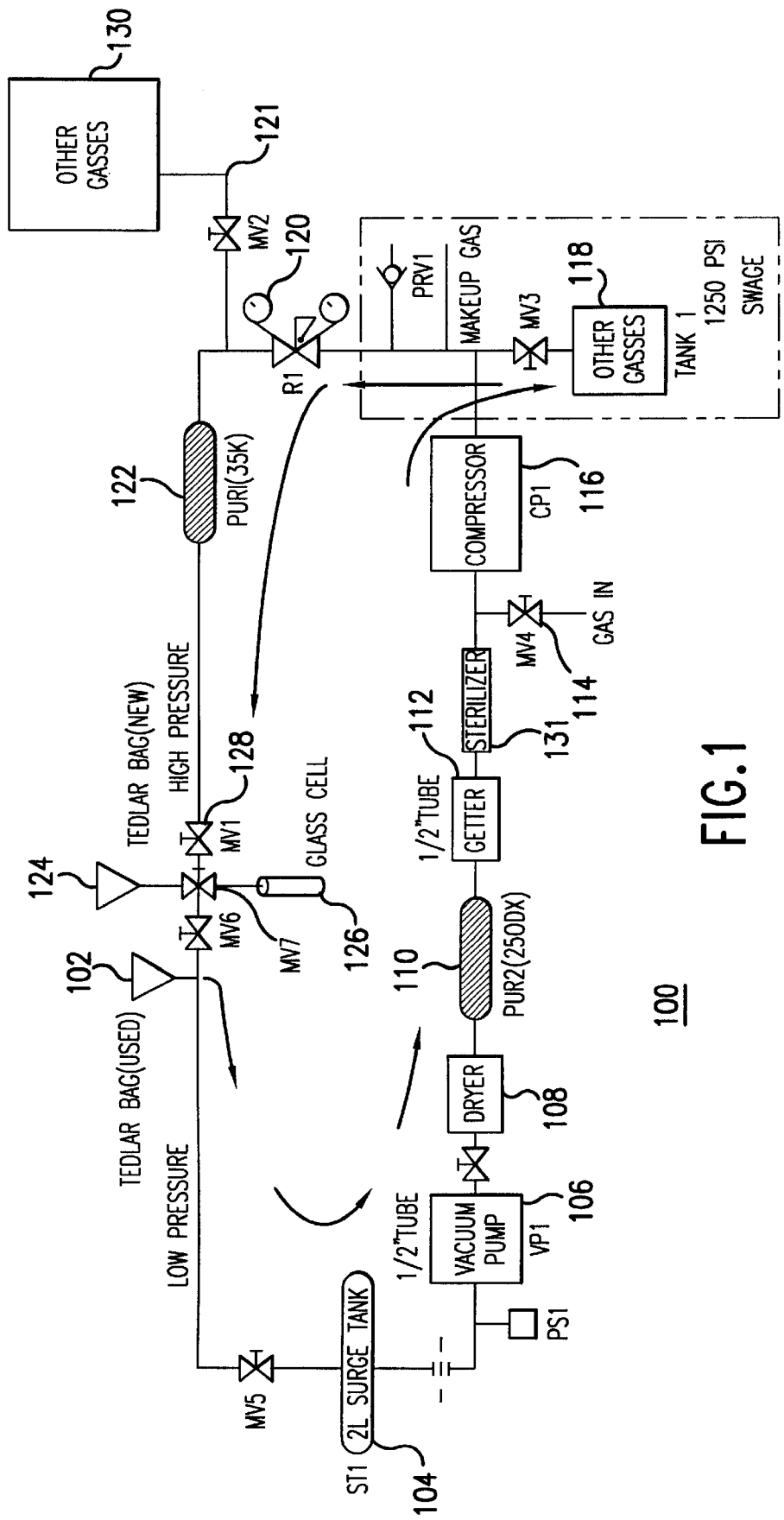
FIG. 1 illustrates one particular recycling system in accordance with the present invention. The reference numerals in the figure designate the following components.

102: first portable container; the particular embodiment illustrated shows a Tedlar bag which contains impure noble gas obtained from a patient that has undergone an MRI procedure; other types of portable containers may also be used or the patient may exhale directly into a port leading into the recycling system;

104: surge tank; the suggested volume is 2 L but this can be altered in accordance with the needs of the operator and in proportion with the other components of the system;

106: vacuum pump;

108: dryer unit; contains material (e.g. desiccant) for the removal of water from the impure gas mixture;

110: purifier unit; contains material for removing $O_2$, and $CO_2$ from gas mixtures, typically activated metal (e.g., activated nickel);

112: getter unit; contains material, e.g., a resin, for removing nitrogen from gas mixtures;

131: sanitizer; this unit is deigned to sterilize gas; e.g., by raising its temperature;

114: valve which may optionally be used to introduce additional noble gas to the storage tank;

116: compressor; used to pump gas into the storage tank; any oil free type of compressor may be used (e.g., a scroll pump);

118: pressurized storage tank (standard tank for high purity gas);

120: computer directed mass flow controller;

121: follow-through tube connected to a second storage tank; can carry additional gasses into the system prior to hyperpolarization; the flow of such gasses would be regulated by an additional mass flow controller (not shown);

130: second gas storage tank designed for high purity inert gas handling;

122: purifier unit;

126: glass cell hyperpolarizing chamber with valve leading to 124;

124: second portable container; can be used to transfer gas to a new patient; alternative designs may also be used, e.g., tubing may lead directly to mask which patient can use for inhalation Other elements shown in the figure are: valves (MV1–MV7); a pressure sensor (PS1); and a pressure release valve (PRV1).

DETAILED DESCRIPTION OF THE INVENTION

The system shown in FIG. 1 is illustrative of the present invention and contains a pump, a compressor, units for purifying gas, and storage tanks. It is designed for recovering a noble gas from the breath of a patient that has been administered such a gas as part of an MRI procedure. Although the invention is described in connection with this particular system, it will be understood that it can be also used with other procedures including, but not limited to MR spectroscopy, nuclear medicine scans, computerized tomography scans, PET scans and in anesthesiology. It can also be used in connection with non-medical procedures and is compatible with any gas. Examples of gasses that may be recycled include $^3$H and other isotopes of hydrogen; $^{129}$Xe and other isotopes of xenon; $^{31}$P; $^{13}$C; $^{23}$Na; and $^{19}$F.

In one preferred embodiment, the recovery process is initiated by a patient breathing into a gas-impermeable container such as a Tedlar bag (102). However, any means for transferring a gas mixture into the system is compatible with the invention. As shown in the figure, the container is connected to a recycling system (100) and then evacuated by means of a vacuum pump (106). The impure mixture of gasses passes through surge tank (104), vacuum pump (106) and dryer (108). The dryer is designed to remove water vapor from the gas mixture and may be comprised of essentially any porous desiccant. After drying, the gasses pass through a purifier (110) which removes carbon dioxide (e.g., using activated metals such as activated nickel) and through a getter (112) which contains material that selectively removes nitrogen. After the getter, there is a valve (114) which is provided to allow additional amounts of a selected gas to be introduced into the system and a sanitizing unit (131). The latter sterilizes the gas by, for example, exposing it to elevated temperatures.

Once it has passed through the dryer, purifier, getter and the sterilizing unit, the only component remaining is the chosen gas. A compressor (116) is used to compress this purified gas so that it may be stored in pressure tank (118) until needed. The compressor is of the non-contaminating type, i.e., it does not contain lubricating oils or seals found in conventional compressors.

In order to recover the stored gas, one or more valves (e.g., valve 128) are opened, and the gas allowed to flow out of the pressure tank (118). Flow rate is regulated by a mass flow controller (120). Additional gasses such as nitrogen, oxygen, and carbon dioxide may be introduced through a flow tube (121) and mixed with the chosen gas. The additional gasses are maintained in other storage units (e.g., 130), and can be regulated with additional mass flow control units, preferably under the direction of computers precisely regulating flow rate. This feature is important in the "closed loop" recycling system described below.

The combination of gasses flows through a purifier (122) into a glass cell (126) where, for example, noble gas is put into a hyperpolarized state by intense laser light, or other means as known in the art. When the gas is sufficiently treated, it is delivered to a fresh container (124) and may then be reused, e.g., it may be administered to a patient whose respiratory system is about to be imaged by MRI.

In another embodiment concerned with MRI imaging, tubes can take the place of the Tedlar bags shown in the FIG. (124 and 102). In this "closed loop" system, the output of the glass cell is routed directly to a person located inside the bore of an MRI device. Likewise, a tube leading away from the person can be attached to the recycling system at the point where bag 102 is attached. Thus, a mixture of gasses may continually flow through the recycling system. If desired, computers controlling mass flow can time the injection of a noble gas to coincide with a person's respiration. In addition, computers can automatically adjust the proportions of the various components in the gas stream.

One advantage of closed-loop systems is that they are more efficient. For example, in the system of FIG. 1, a certain amount gas remains in Tedlar bags, even after they are evacuated by a vacuum pump, and a certain amount is lost in transferring the bags to and from the system. A closed-loop system avoids such inefficiencies by using a tight fitting mask to seal the person's respiratory system from the atmosphere. Thus, the opportunity for gas to escape is greatly reduced.

Helium 3 ($^3$He) and Xenon 129 ($^{129}$Xe) are examples of noble gasses that may be recovered in the recycling systems described above. However, other gasses, particularly other noble gasses, may be recovered as well. It should also be recognized that, although recovery systems have been described in the context of medical procedures, they are also compatible with industrial applications of MRI technology (e.g., the imaging of rock samples). In fact, any procedure which utilizes noble gasses that can later be trapped can benefit from the recycling device described above.

EXAMPLES

Methods

The present example describes a recycling device consisting of modules that can easily be adapted to purify gas for different applications. The system purifies noble gas by removing contaminants such as $O_2$, $N_2$, hydrocarbons, CO, $CO_2$, $H_2O$ and other paramagnetic impurities. A high-energy laser then polarizes the gas in a pump cell.

For imaging humans, polarized gas is transferred into a container (e.g. a flexible Tedlar™ bag) for the subject to breathe prior to or during MRI. After the imaging session, the patient exhales the used gas into a bag where it is transferred back into the recovery side of the device. Gas is delivered and advanced through the device using a series of commercially available vacuum and pressurization pumps, all designed for ultra-clean service. Impurities are removed by passing the gas through a series of system components such as sieves, getters, purifiers and cryogenic separators. Purified noble gas is then stored in a high-pressure cylinder where, if desired, it can be mixed or diluted with other gases such as $N_2$, or $^4$He. On demand, gas may be removed from storage, optionally mixed with other gases, and then purified (e.g., by means of a sterile filter for medical purposes) before again entering the polarizing chamber. Flow from storage can be regulated using mass flow controllers and a monitoring system may be used to measure gas purity. At present, monitors are capable of measuring the moisture content of gas to parts per billion as an estimate of purity.

Hyperpolarized noble gases (e.g., xenon and helium) can also be transferred to a patient in the bore of the scanner in a closed loop without the use of bags or other portable containers. This is accomplished by connecting a tube from the noble gas polarizer to the patient and from the patient to the recycling device. Computer controlled pneumatic valves may be used to control the flow of the hyperpolarized gas through this system. Gases can also be premixed (e.g., 1% Xe; 1% $N_2$ and 99% $^4$He) as used by a commercial polarizer (e.g. MITI, Durham, USA).

The principles and devices discussed above can be used, not only in MRI but also in other medical and non-medical applications, e.g., to recycle gas for NMR studies of rocks or other materials and for industrial applications. Recycled gas can also be dissolved or encapsulated in biocompatible carrier agents for intravascular injection.

Results and Discussion

1Hyperpolarized noble gas MRI is a rapidly growing imaging modality with unmatched diagnostic capabilities for lung disorders. The gas recycling device described above should substantially reduce the cost of hyperpolarized gas generation and, by extension, the cost of these diagnostic procedures. The recycling device may also be used in the hyperpolarized gas MRI of rock samples (used in oil well logging), in materials science (e.g. to determine the porosity of materials) and in other industrial applications.

What is claimed is:

1. A method for recycling a chosen gas used in a medical procedure, comprising:

a) retrieving a gas mixture from a first patient, wherein said gas mixture includes said chosen gas;

b) inserting said gas mixture into a recycling device;

c) passing the gas mixture through a dryer unit to remove water vapor from the gas mixture;

d) passing the gas mixture through a getter to remove non-chosen gasses in the gas mixture, wherein only the chosen gas remains;

e) storing the chosen gas for later use;

f) removing the chosen gas from storage;

g) transferring the chosen gas to a cell, wherein it is prepared for delivery to a second patient; and h) supplying the gas prepared in step g) to said second patient.

2. The method of claim 1, wherein said medical procedure is diagnostic MRI; said chosen gas is a noble gas; and wherein, after recovery, said noble gas is prepared for delivery to said second patient in step g) by putting it in a hyperpolarized state.

3. The method of claim 1, wherein said chosen gas is selected from the group consisting of: an isotope of Xe; an isotope of He; $^{31}$P; $^{13}$C; $^{23}$Na; and $^{19}$F.

4. A device for recycling a chosen gas, comprising:

a) a first portable container (102) connected to a first end of a first gas line;

b) a vacuum pump (106), connected to the second end of said first gas line;

c) a getter (112), connected to said vacuum pump;

d) a storage container (118), connected to said getter and to a first end of a second gas line;

e) a mass flow controller (120) for regulating the amount of said gas that flows from said storage container and which is connected to the second end of said second gas line;

f) a purifier (122) connected to said mass flow controller;

g) a cell (126) for preparing said gas for delivery to a patient and connected to said purifier; and h) a second portable container (124) for receiving hyperpolarized noble gas from said cell.

5. The device of claim 4, wherein said gas is prepared for delivery to a patient in step g) by putting said gas into a hyperpolarized state.

6. The device of claim 4, further comprising:

a) a dryer (108) connected to said vacuum pump; and b) a second purifier (110) connected to said dryer (108) and to said getter (112).

7. The device of claim 6, further comprising a sanitizer (131) for sterilizing gas, said sanitizer being connected to said getter (112) and to said storage tank (118).

8. The device of claim 7, further comprising a compressor (116) connected to said getter (116) and to said storage tank.

9. The device of claim 8, further comprising:

a) a surge tank (104) connected to said first portable container (102) and to said vacuum pump (106); and b) a valve (114) for introducing additional noble gas into said storage tank (118), said valve being connected to said sanitizer (131) and to said compressor (116).

10. The device of claim 9, further comprising a second a second storage tank (130) that may be used to mix additional gasses with said noble gas prior to hyperpolarization, said second storage tank being connected to said purifier (122) and to said mass flow controller (120).

11. A method of recycling a chosen gas comprising introducing an impure mixture of said chosen gas into the device of any one of claims 4–10.

12. The method of claim 11, wherein said chosen gas is a noble gas.

13. The method of claim 11, wherein said chosen gas is selected from the group consisting of: an isotope of Xe; an isotope of He; $^{31}P$; $^{13}C$; $^{23}Na$; and $^{19}F$.

14. An MRI imaging machine comprising a device for recycling a chosen gas, wherein said device for recycling a chosen gas is positioned so that the retrieval of said chosen gas occurs at an exit port in the bore of the scanner of said MRI machine; said chosen gas is transferred out of said device at an entry port in the bore of the scanner of said MRI machine; and wherein said device for recycling a chosen gas comprises:

a) means for recycling a mixture of gases containing said chosen gas and introducing said mixture of gases into said device;

a) means for propelling the gases introduced in step a) through said device;

c) means for purifying chosen gas as it is propelled through said device;

d) means for storing chosen gas purified by the means of step c);

e) means for removing chosen gas from the storage means of step d) and for regulating the amount of gas that flows from said storage means;

f) means for transforming gas that has been removed from the storage means of step d) into a state for delivery to a patient; and g) means for transferring the gas prepared in step f) out of said device.

15. The MRI machine of claim 14, wherein said chosen gas is a noble gas that is transformed into a state for delivery to a patient by putting it into a hyperpolarized state.

\* \* \* \* \*

UNITED STATES PATENT AND TRADEMARK OFFICE
CERTIFICATE OF CORRECTION

| | | |
|---|---|---|
| PATENT NO. | : 6,471,747 B1 | Page 1 of 1 |
| APPLICATION NO. | : 09/598428 | |
| DATED | : October 29, 2002 | |
| INVENTOR(S) | : Venkatesh et al. | |

It is certified that error appears in the above-identified patent and that said Letters Patent is hereby corrected as shown below:

In column 1, lines 10-13, of the issued patent, the paragraph after "Statement of Government Support" should be corrected to specify the source of funding. The corrected paragraph should read as follows:

-- This invention was made with Government support under Grant No. BES9617342 awarded by the National Science Foundation. The U.S. Government therefore has certain rights in the invention. --

Signed and Sealed this

Eighteenth Day of August, 2009

David J. Kappos
*Director of the United States Patent and Trademark Office*